United States Patent
Mann et al.

(10) Patent No.: US 9,005,140 B2
(45) Date of Patent: Apr. 14, 2015

(54) WEIGHT MONITORING APPARATUS, WEIGHT MONITORING SYSTEM, AND RELATED METHODS THEREOF

(75) Inventors: Kenneth A. Mann, Jamesville, NY (US); Nathaniel R. Ordway, Cicero, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 714 days.

(21) Appl. No.: 12/740,861

(22) PCT Filed: Oct. 31, 2008

(86) PCT No.: PCT/US2008/081991
§ 371 (c)(1),
(2), (4) Date: Aug. 18, 2010

(87) PCT Pub. No.: WO2009/059134
PCT Pub. Date: May 7, 2009

(65) Prior Publication Data
US 2010/0305478 A1 Dec. 2, 2010

Related U.S. Application Data

(60) Provisional application No. 60/984,759, filed on Nov. 2, 2007.

(51) Int. Cl.
*G01G 19/44* (2006.01)
*A61B 5/103* (2006.01)
*A61B 5/00* (2006.01)
*A61B 5/117* (2006.01)

(52) U.S. Cl.
CPC .............. *G01G 19/44* (2013.01); *A61B 5/1036* (2013.01); *A61B 5/1038* (2013.01); *A61B 5/6829* (2013.01); *A61B 2562/0247* (2013.01); *A61B 2562/043* (2013.01); *A61B 2562/046* (2013.01)

(58) Field of Classification Search
CPC .... A61B 5/1036; A61B 5/1038; A61B 5/112; A61B 5/6807; A61B 5/6812; A61B 5/6829
USPC .......................................... 600/587, 592, 595
See application file for complete search history.

(56) References Cited

U.S. PATENT DOCUMENTS

| | | | |
|---|---|---|---|
| 3,702,999 A | 11/1972 | Gradisar | |
| 5,253,654 A | 10/1993 | Thomas et al. | |
| 5,357,696 A * | 10/1994 | Gray et al. | 36/136 |
| 5,408,873 A * | 4/1995 | Schmidt et al. | 73/862.625 |
| 5,636,456 A | 6/1997 | Allen | |
| 5,673,500 A * | 10/1997 | Huang | 36/136 |
| 6,122,846 A * | 9/2000 | Gray et al. | 36/136 |

(Continued)

OTHER PUBLICATIONS

International Search Report and Written Opinion from PCT Application No. PCT/US2008/081991 dated, Jan. 22, 2009.

*Primary Examiner* — Adam Eiseman
(74) *Attorney, Agent, or Firm* — Hoffmann & Baron, LLP (57) ABSTRACT

The present invention relates to embodiments which enable repetitive measurement and monitoring of the load applied to an apparatus, in a system, and/or by a method which may exceed a predetermined threshold of weight. Specifically, the present invention relates to weight monitoring apparatus, locomotion monitoring apparatus, a gait-response apparatus, a weight monitoring system, and a therapeutic load monitoring method.

21 Claims, 8 Drawing Sheets (56) References Cited

U.S. PATENT DOCUMENTS

| | | |
|---|---|---|
| 6,405,606 B1 | 6/2002 | Walczyk et al. |
| 6,836,744 B1 * | 12/2004 | Asphahani et al. ........... 702/141 |
| 7,426,873 B1 * | 9/2008 | Kholwadwala et al. ........ 73/818 |
| 8,384,551 B2 * | 2/2013 | Ross et al. ................. 340/573.7 |
| 8,639,455 B2 * | 1/2014 | Horst et al. ..................... 702/44 |
| 2007/0050271 A1 * | 3/2007 | Ufford et al. ................... 705/28 |
| 2010/0145239 A1 * | 6/2010 | Kudoh et al. ................... 601/34 |

* cited by examiner

WEIGHT MONITORING APPARATUS, WEIGHT MONITORING SYSTEM, AND RELATED METHODS THEREOF

CROSS-REFERENCE TO RELATED APPLICATIONS

This application is the National Stage of International Application No. PCT/US2008/081991, filed Oct. 31, 2008, which claims the benefit of U.S. Provisional Application No. 60/984,759, filed Nov. 2, 2007, the contents of which are incorporated by reference herein in their entireties.

FIELD OF THE INVENTION

The present invention relates to embodiments which enable repetitive measurement and monitoring of the load applied to an apparatus, in a system, and/or by a method which may exceed a predetermined threshold of weight. Specifically, the present invention relates to weight monitoring apparatus, locomotion monitoring apparatus, a gait-response apparatus, a weight monitoring system, and a therapeutic load monitoring method.

BACKGROUND OF THE INVENTION

There are many medical symptoms and physical conditions which, in one way or another, limit the mobility of the ailing person. For these persons (referred to herein as subjects or users) affected with medical symptoms which prevent them from balancing, standing, walking, gait, or locomoting in a normal and/or ideal fashion, it may be difficult to teach these people to correctly walk while applying a limited amount of weight to the lower extremities, such as the person's foot or feet. It is commonplace for healthcare professionals to advise or instruct users not to exceed a certain weight limit or load on their feet, commonly referred to as limited weight bearing, to prevent injury or facilitate healing. In particular, the user may be advised by a healthcare professional to perform certain exercises, while maintaining the reduced weight pressure on the user's foot. Sometimes, healthcare professionals may prescribe the use of crutches or a cam boot to a patient, which may be accompanied by instruction to reduce the pressure exerted on the foot while in use.

However, many subjects have difficulty performing exercises as instructed by health care professionals. Users performing such exercises typically exert too much weight on the foot, which can cause further damage or slow the healing process. Thus, a device that monitors and provides feedback as to the pressure level exerted on the foot is useful to those in need, so that the user can be aware of when they have exceeded the recommended pressure level, and can reduce the pressure. There are currently several in-shoe monitoring devices that monitor pressure distributions during walking using thin film inserts; however, devices currently marketed have not been widely adopted clinically because of their relatively high cost, especially for those devices incorporating electrical components, and many fail to provide a suitable tactile feedback to the user. In addition, many devices include several components, such as components placed proximal to the foot as well as components clipped onto the user's body. Other devices incorporate wires or other electrical signal-generating aspects, batteries, transmitters, and other complex equipment. These devices are not only cumbersome and expensive, but are additionally prone to malfunction.

One type of weight bearing indicator has been developed as a low cost alternative, which includes a free-standing mechanical snap-dome device placed within footgear, providing both audible and tactile biofeedback to the subject, such as that summarized in U.S. Pat. No. 6,405,606. However, such snap-dome devices suffer from severe limitations. One particular limitation is that if force is not applied directly through the center of the device (directly downward), the dome may not properly snap, and thus will not register or provide feedback regarding the applied force. In fact, this limitation occurs fairly often, since the distribution of the force on the bottom of the foot changes as the user progresses from heel-strike to toe-off during normal ambulation. As a result, users that perform instructed or advised exercises with these snap-dome devices often apply excessive weight loads at an angle in the foot bed which does not pass through a traditional snap dome loading device. The snap-dome device does not provide audible or tactile feedback, which may deceive the user into thinking that they are complying with medical advice while the unmeasured excessive loads may, in fact, injure or prolong the recovery of the user. Further, the tactile or acoustic alarms of a free-standing snap-dome device may slip out of place or otherwise move during typical locomotion.

Based on the shortcomings of the devices currently used today, there exists a need for a full-sole weight bearing apparatus which will allow the user to monitor the pressure applied to the foot safely and securely, and which overcomes the problems associated with such weight bearing apparatuses currently marketed.

SUMMARY OF THE INVENTION

A first aspect of the present invention provides a weight monitoring apparatus, including: a substantially rigid first member having a bottom surface; a second member having a top surface; at least two sensors, the sensors being disposed located at a position between the first member and the second member and configured to associate to the first member such that the top edge of each of the sensors is in contact with the bottom surface of the first member.

A second aspect of the present invention provides a locomotion monitoring apparatus, including: a plurality of sensors; and a substantially flat base member having a first surface and a second surface; where at least one edge of each of the plurality of sensors maintains contact with the first surface of the base member.

A third aspect of the present invention provides a gait-response apparatus, including: a substantially flat first member having a first surface; a substantially flat second member having a second surface; a plurality of sensors, where at least one edge of each of the sensors is configured to associate with the first surface of the first member, and where at least a second edge of each of the sensors is configured to associate with the second surface of the second member; where the apparatus provides a detectable feedback to a user if a predetermined mechanical force threshold is exceeded on at least one of the sensors.

Another aspect of the invention provides a locomotion measuring and monitoring apparatus, including: a substantially rigid first member having a surface; at least two sensors, each sensor having a first and second edge, where the first edge of each of the sensors maintains contact with the surface of the first member; a second member having a second surface, where the second edge of each of the sensors maintains contact with the second surface of the second member; and a lever disposed at a location between the first member and the second member such that the lever and the sensors prevent the first member from contacting the second member.

BRIEF DESCRIPTION OF THE DRAWINGS

The present invention is described in detail below with reference to the drawings in which.

DETAILED DESCRIPTION OF THE INVENTION

The subject invention provides a monitoring apparatus and methods of use, which provides feedback to a user when a certain force or weight has been applied thereon. In a preferred embodiment, the apparatus is to be worn on the foot, thus measuring the pressure or weight which is placed on the user's foot, but it is contemplated that the apparatus can provide feedback to the user in any situation where force levels are to be monitored and maintained. In one aspect, health care professionals may instruct users to walk with limited loading of the foot with toe-touch weight bearing where the force applied to the foot from the floor not to exceed a certain percentage of the user's body weight. As used herein, the term "non-weight bearing" refers to situations where the foot should desirably not touch the floor. Also as used herein, the term "partial weight bearing" refers to situations where loads may be increased above the weight felt when the toe touches the floor ("toe-touch weight bearing"), but less than full weight bearing where loads on the foot during ambulation can exceed the subject's body weight. As may be appreciated by one of skill in the art, there is a need in many situations to monitor and control the weight level exerted onto the user's foot.

During gait (also referred to as ambulation), peak loads are applied to the foot at two main times: during heel strike and at toe-off. The heel usually strikes the ground surface first with a large force, followed by midstance where the surface reaction force is diminished, followed by a toe-off where forces rise again. By placing pressure-detecting sensors that measure heel strike forces and toe-off forces, the present invention is capable of detecting these two most important phases of the gait cycle. As will be explained in more detail below, another aspect of the present invention incorporates a plate-like member, which helps in maintaining directional force onto the sensors, as well as an optional stability bar, which acts as a fulcrum for the plate-like member, helping to direct loads through the pressure-detecting sensors. The stability bar may be placed at any location with respect to the user's foot so that it does not interfere with heel strike and toe-off loading. In a preferred embodiment, the stability bar is disposed at a location substantially in the middle of the user's foot (i.e., between the toes and the heel). Due to the construction of the present invention, forces need not be applied directly over the sensor in order to for the sensor to detect the pressure. This construction allows off-axis loading and changing distributions of loading to be captured by the force sensor, and marks a substantial improvement over sensor devices currently marketed today.

Figure 1:
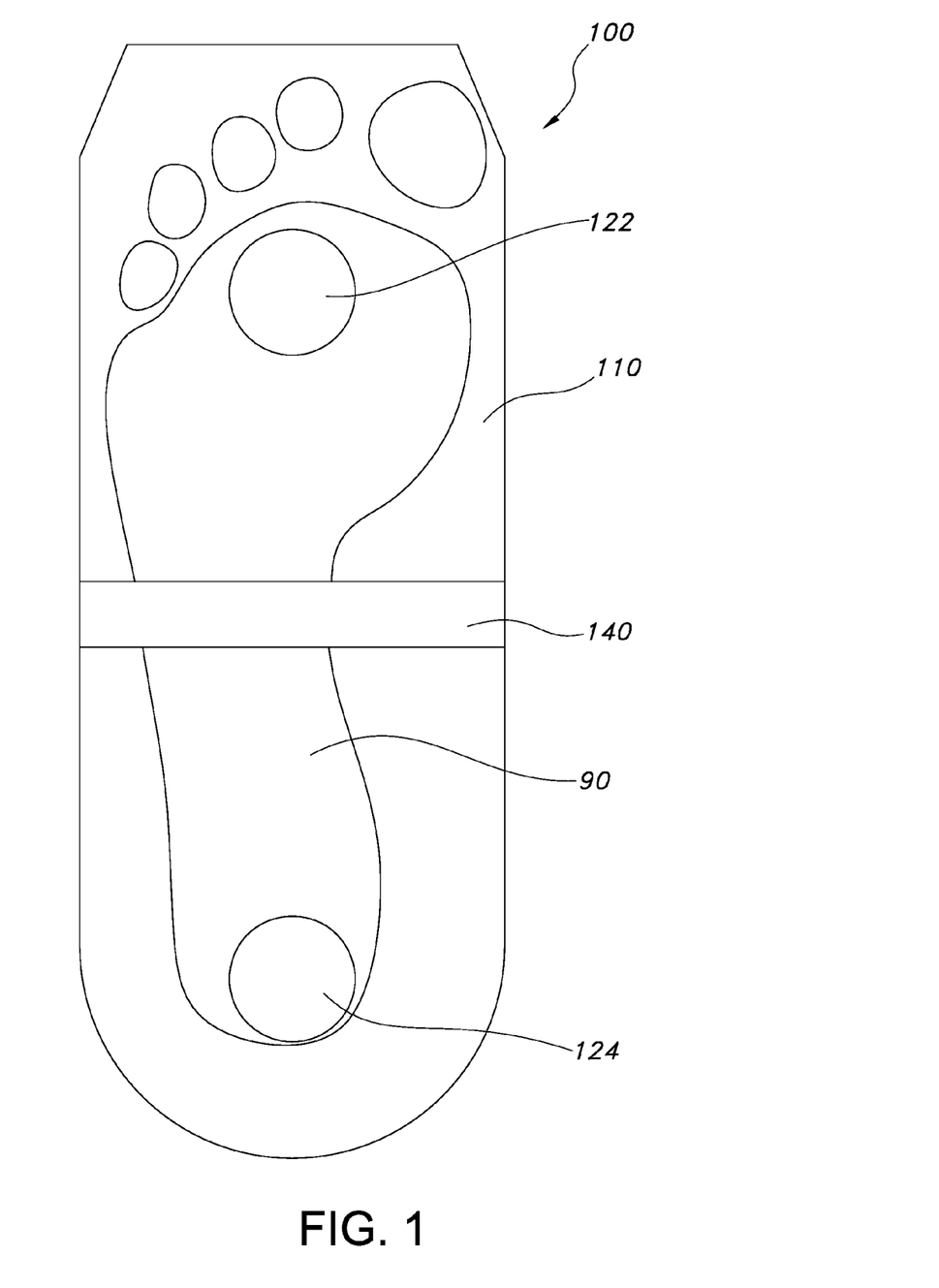
FIG. 1 depicts a cut away top view of an example of an embodiment of the weight monitoring apparatus of the present invention.
Figure 5:
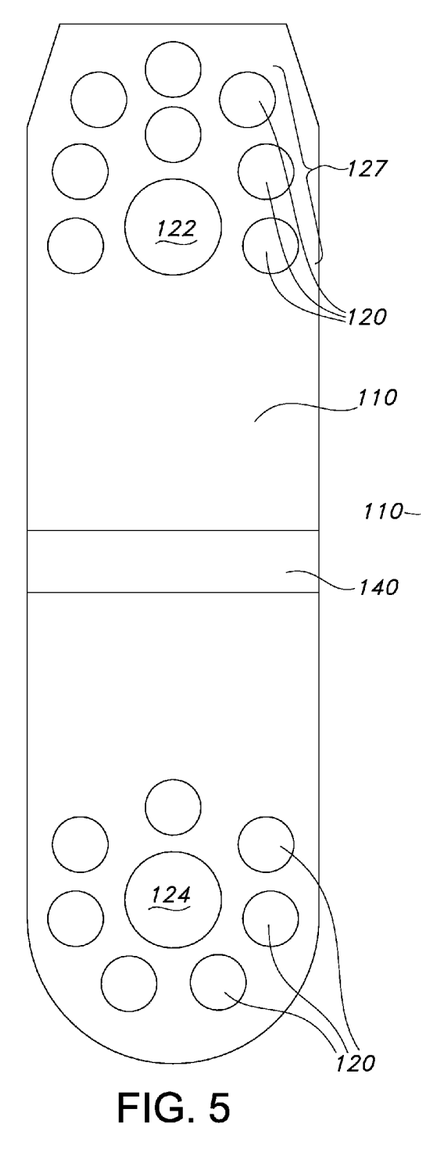
FIG. 5 depicts a top cut away plan view of an example of an embodiment of the gait-response apparatus.

Reference is made to the Figures set forth herein. With reference to FIG. 1, the apparatus includes at least two sensors 120 disposed therein. In some embodiments, such as that depicted in FIGS. 5 and 6, the apparatus may include a plurality 127 of sensors 120, as will be discussed and disclosed below. As used herein, the term "sensor" includes any device that is capable of detecting changes in pressure. It is designed to encompass mechanical sensors as well as electrical sensors.

Figure 1A:
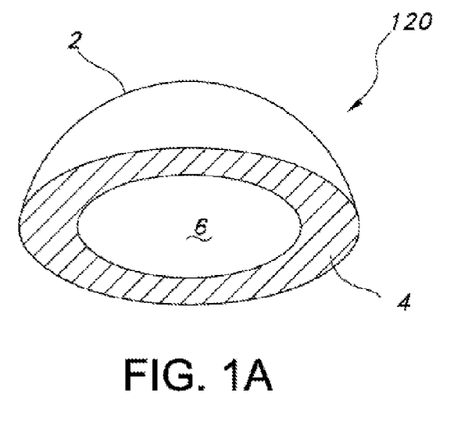
FIG. 1A is a perspective view of one embodiment of a sensor of the present invention.

In a preferred embodiment, the sensor is a pressure-detecting mechanical sensor, which has an open dome construction as seen in FIG. 1A. One such sensor 120 includes a first edge 2 and a second edge 4. One embodiment of the sensor is an open dome construction, where the first edge 2 forms the top of the dome, the second edge 4 forms the bottom of the dome, and there is an open middle space 6 therebetween. In this arrangement, pressure applied to the first edge above a certain level will cause the dome to collapse, providing a snap, which may be both heard and felt by one in contact with the sensor. Other arrangements are contemplated, such as those having other geometric shapes (i.e., boxed, spherical, etc.). The sensor 120 may be any size desired, such that it can achieve the goal of monitoring force applied by a user. In a preferred embodiment, the sensor is a fairly small snap-dome device, which has a diameter of about 30-50 mm, and more particularly a diameter of about 40 mm. Larger or smaller sensors 120 may be used in conjunction with the device described herein. Similar mechanical sensors include those described in U.S. Pat. No. 6,405,606, which is incorporated by reference herein.

In a preferred embodiment, the apparatus 100 includes at least one sensor 120 disposed at a location proximal to the toe region 122 of the user and at least one sensor 120 disposed at a location proximal to the heel region 124 of the user. In such a manner, both heel strike and toe-off forces may be measured in a foot to provide for more effective, efficient, and practical load measurement. However, it should be understood that the apparatus 100 is not limited to using two sensors 120. In some embodiments, the apparatus 100 may including only one sensor 120 disposed at any location, including the toe region 122 or the heel region 124, or at a location therebetween. In some embodiments, there is disposed a plurality 127 of sensors 120 at only one region of the foot 90. In some embodiments, there may be disposed a first member 110, which is substantially flat and substantially rigid, forming a loading plate. The first member 110 preferably contacts the first edge 2 of each sensor 120, in such a fashion that each sensor 120 is located on the same side of first member 110.

In one desirable aspect of the invention, the apparatus 100 includes a support bar 140. The support bar may be any shape or design desired, and preferably is a cylindrical or elongated box shape. The support bar 140 spans the width of the user's foot, and is preferably disposed at a location between at least two sensors 120. In a desired embodiment, the apparatus 100 includes at least one sensor 120 disposed at the toe region 122 and at least one sensor 120 disposed at the heel region 124 of the user's foot 90, and further includes a support bar 140 disposed therebetween. The support bar 140 is preferably disposed such that it is in contact with the first member 110 and is disposed on the same side of the first member 110 as the sensors 120. In this fashion, the support bar 140 acts as a lever, allowing pressure from the user's foot 90 to be applied to either the toe region 122 or the heel region 124 more effectively.

The various weight, load, and gait-response apparatuses described herein may be used by a user to measure the passive mechanical forces which are applied to the apparatus during both the heel strike and toe-off partial weight bearing. The apparatuses described herein may be used in conjunction with various footwear devices, including in a boot, such as a plastic fracture boot commonly referred to as a "cam boot". In other embodiments, the apparatuses described herein may be used in conjunction with other types of foot coverings, including braces, casts, and boots. The various embodiments of the apparatuses may be placed in the footwear or they may be constructed as a part of the footwear. The apparatus 100 may include a foam covering, which encompasses the sensors 120. In some embodiments, the apparatus 100 may be an insert that is placed within the footwear, such as by removing a portion of the padding material from the footwear and instead, placing the apparatus 100 into the desired location. As used herein, the desired location is on the bottom of the footwear, such that the user's foot rests on top of the apparatus.

The present invention provides various exemplary embodiments which may aid in the control of load transfer on a user's foot in a consistent manner. As such, the subject may be provided with an efficient, effective, and consistent monitoring and response system to facilitate proper weight loading onto one or both of the subject's feet. The embodiments of the apparatus may be used to aid patients in achieving partial weight bearing conditions as may be prescribed by a health care professional following, for example, various medical limitations of the user. Such medical limitations may include, for example, surgery to the lower extremities, injury to the lower extremities, medical diagnosis of cerebral palsy (which symptomatically causes difficulty in balance and/or walking); recovering stoke victims, loss of balance and/or dizziness, aid in prosthesis therapy/training, ideal foot placement in athletics training, physical therapy, and other various physical conditions or diagnoses. In addition, the various embodiments of the present invention may be utilized in combination with a shoe, boot, cast, walking cast, brace, or plastic fracture boot or cam boot without medication. That is, the various advantages of the present invention incorporate the benefits of the snap dome design with a more robust package that can provide consistent and repeatable tactile and audible feedback once a predetermined weight threshold is exceeded. The various embodiments of the present invention are put forth herein in a non-limiting, exemplary nature with reference to accompanying figures.

The various embodiments of the present invention provide apparatuses which may control load transfer in a much more effective and consistent manner compared with a design incorporating a free-standing snap dome device or a design wherein the snap dome device is not in conjunction with a loading plate.

Figure 2:
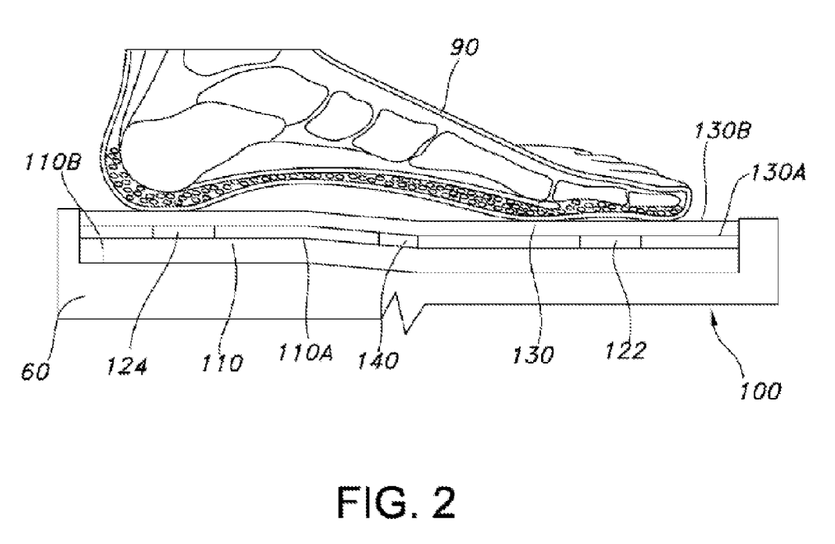
FIG. 2 depicts a cut-away side view of an example of an embodiment of the weight monitoring apparatus of the present invention in situ.

One aspect of the present invention, such as that depicted in FIG. 2, includes the weight monitoring apparatus 100 having a substantially flat first member 110, at least two sensors 120, a substantially flat second member 130, and a support bar 140. The first member 110 may be configured to substantially conform to a surface. The surface may be the ground, a floor, or an inner bottom portion of footwear, including, for example, a shoe, a boot, a cast, a walking cast, a brace, or a cam boot. The first member 110 may be constructed of one or more materials which may provide a stable and relatively stiff base for the various other elements of the apparatus, such that the first member 110 may be substantially unyielding when a load is applied thereon. Such materials may include plastic, epoxy, carbon fiber, metal, wood, and composite materials such as fiber glass and glass filled plastics, for example. Although the first member 110 should be substantially flat and rigid, it will be understood that the first member 110 may have some degree of yield, which allows for comfort to the user while the user is wearing the apparatus 100 and walking.

The apparatus 100 includes at least two sensors 120, which may include, for example, a first sensor disposed at a location proximal to the toe region 122 of the user's foot 90 and a second sensor 124 disposed at a location proximal to the heel region 124 of the user's foot 90. However, the apparatus 100 may include more than two sensors 120. Each of the at least two sensors 120 may have, for example, a substantial dome configuration as described above, such as a hemisphere or a shape having a parabolic or arc shaped cross-sectional profile.

The at least two sensors 120 may be made of one or more suitable materials and specifically designed or otherwise known to retain the substantial dome configuration under and up to a certain predetermined threshold of weight or load. As explained above, once the predetermined threshold is exceeded, the substantial dome configuration of the sensor 120 may collapse, shrink, cave, or otherwise lose shape in response to the excessive load. Upon this caving, collapsing, sinking, or otherwise lowering of the at least one of the sensors, the change in shape of the sensor may in turn alert the user to a change in height or orientation of the foot or lower extremity. In other embodiments, the change in configuration of at least one of the sensors 120 may be accompanied, for example, by an audible sound, such as a click or snap, an acoustic resonance, or one or more tactile signals or alarms to a user or subject that a predetermined threshold has been reached.

The apparatus preferably includes a second member 130, which may be configured to associate with the at least two sensors 120. The second member 130 is preferably a substantially flat, plate like surface, having a bottom surface 130A and a top surface 130B. In the preferred embodiment, the domed edge 2 of each sensor 120 is in contact with the bottom surface 130A of the second member 130. Also, in the preferred embodiment, the bottom surface 4 of the sensor 120 is in contact with the top surface 110A of the first member 110. This manner forms a sandwich-like design depicted in FIG. 2.

The sensor(s) 120 may be removably attached, fixably attached, attached, or integral to either the first member 110, the second member 130, or both. That is, the sensors 120 may be glued, nailed, screwed, snapped, hooked, magnetized, welded, adhered, fused, buttoned, or otherwise associated with the first member 110 and/or the second member 130. As another example, the sensors may be fit onto or through the first member 110 and/or the second member 130 during one or more steps of the manufacturing process such that the apparatus 100 is integral in appearance and use to a subject or user.

In this embodiment, the user's foot 90 may rest on the top surface 130B of the second member 130. The user's foot 90 may then exert pressure in a downward manner, at least one of the heel region 124 or the toe region 122 of the foot 90 (or both regions simultaneously). This transmits the pressure from the second surface 130 to the sensor 120 onto which the force is applied. The sensor 120 is stopped from further downward movement by the first member 110. In such a manner, when the predetermined weight threshold of the one or more of the at least two sensors 120 is exceeded, the sensors 120 may collapse and send a signal to a user as described above. Importantly, in this configuration, the second member 130 is associated with the at least two sensors 120 such that various angular loads may be accepted by the second member 130 and likewise distributed onto one or more of the at least two sensors 120. As is appreciated by one of skill in the art, during normal walking, the user's foot 90 does not always exert force in a 90° angle to the surface on which the user is walking. Inclusion of the second member 130 allows for the user's foot 90 to apply force in various directions, while still exerting a proper directional force from the second member 130 to the sensor(s) 120. Also, it should be noted that the second member 130 may be semi-rigid such that load may transfer through the at least two sensors 120, allowing the second member 130 to remain somewhat flexible, providing comfort to the user. In embodiments wherein there are disposed a plurality 127 of sensors 120, exertion of force on the second member 130 may allow for angular load transfer to one or more of the various sensors 120 in the plurality 127 of sensors 120 in a much more controlled fashion than a single free-standing snap dome sensor. This may in turn make the desired monitoring of excessive force much more robust as the pressure from the foot 90 during weight bearing activities may be more reliably transferred to the first member 130.

The predetermined threshold of weight or load may be a function of one or more of the following, including: the flexural modulus of the sensor material or combination of materials, the strength of the geometric configuration and shape orientation, the amount and type of force exerted upon one or more of the sensors, and/or the presence of a fulcrum in the apparatus 100. In one embodiment, the apparatus 100 includes a support bar 140 disposed located, for example, between at least two of the sensors 120. In addition, the support bar 140 may be disposed at a location between the first member 110 and the second member 130. As explained above, the sensors 120 described herein may be a passive mechanical design, an electromechanical design, or a combination thereof.

Figures 3, 4:
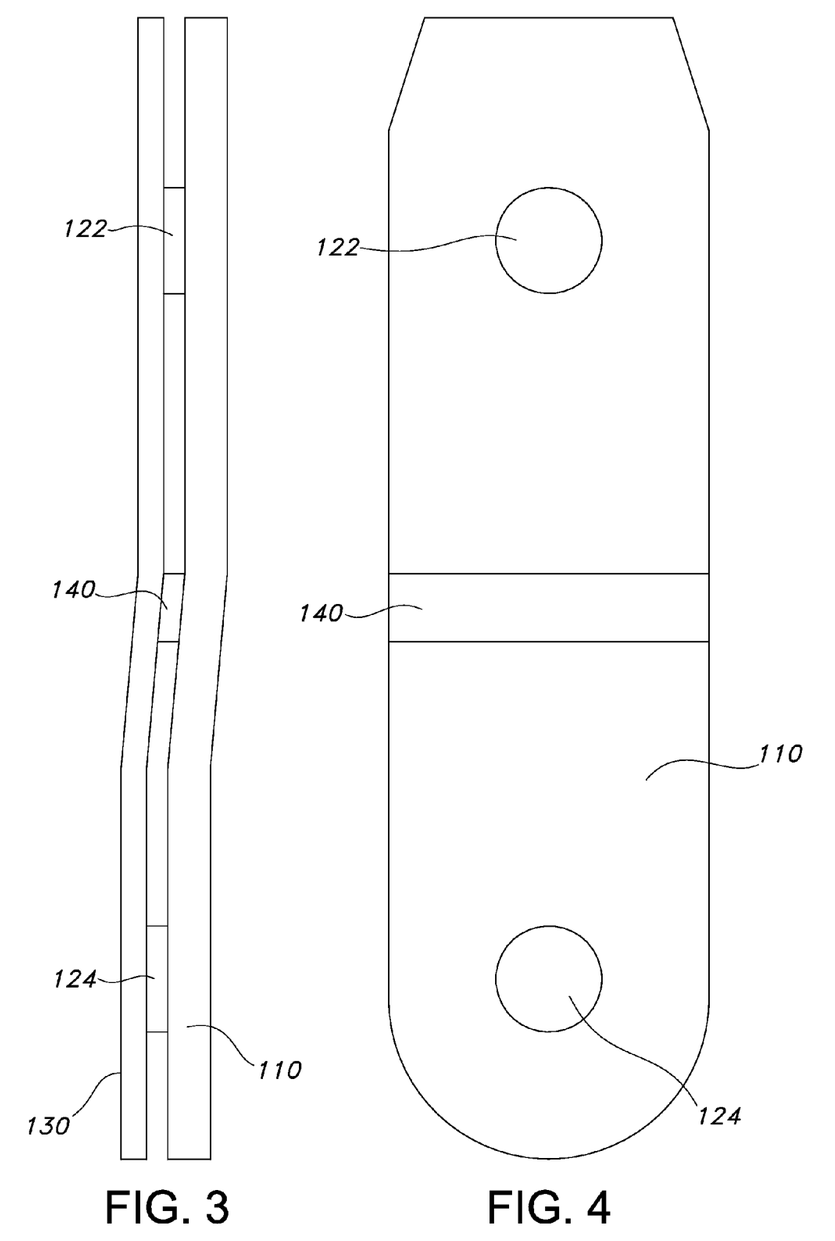
FIG. 3 depicts a cut away side view of an embodiment of the weight monitoring apparatus of the present invention.
FIG. 4 depicts a top plan cut away view of an example of an embodiment of the weight monitoring apparatus of the present invention.

As seen more clearly in FIG. 3, the support bar 140 of the weight monitoring apparatus 100 may be configured to associate, for example, between the first member 110 and the second member 130, between a first sensor 120 disposed at the toe region 122 and a second sensor 120 disposed at the heel region 124, or between both sets of members and at least two sensors. In this fashion, the support bar 140 and the at least two sensors 120 (which are sandwiched between the first member 110 and second member 130) may prevent or at least substantially hinder the first member 110 from contacting the second member 130. In this manner, the support bar 140 may function, for example as a fulcrum, while the second member 130 functions as a lever. The support bar 140 may be constructed of one or more sturdy materials, including plastics, metals, wood, foam, or combinations thereof. Further, the support bar 140 may be of any desired size, shape, and dimension which may be advantageous for the weight monitoring apparatus 100. The support bar 140 may be solid, porous, or hollow configuration in one or more portions of the support bar 140. The support bar 140 may be placed in one or more various orientations, or alternatively, angled in one or more directions to facilitate a gait, locomotive analysis, diagnostics, or therapy of a subject or user. The support bar 140 may provide stability to the second member 130 for off axis loading. Also, the support bar 140 may act as a pivot point for cantilever-type loading.

Figure 6:
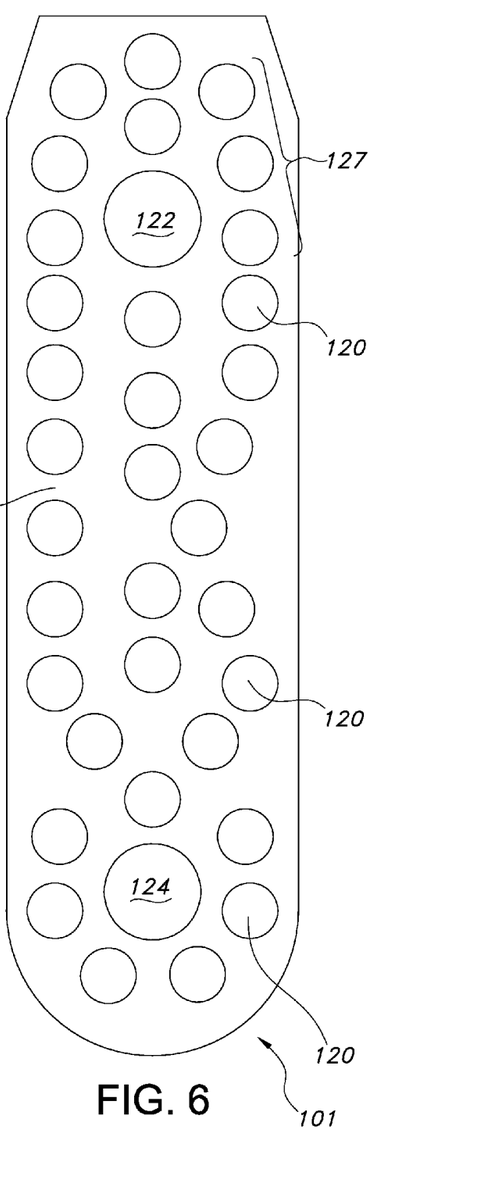
FIG. 6 depicts a top cut away plan view of an example of an embodiment of the locomotive monitoring apparatus.

Another aspect of the present invention, such as that depicted in FIG. 6, may include a gait-response apparatus 101. The gait-response apparatus 101 may include, for example: a first member 110, and a plurality 127 of sensors 120 disposed throughout the apparatus 101. As described above, the gait-response apparatus 101 may further include a second member 130, and a support bar 140. The first member 110, may be configured to substantially conform to a surface, such as the ground or a floor. The first member 110 may include the features and characteristics as previously disclosed and discussed.

The plurality 127 of sensors 120 may have a substantial geometric configuration. Each of the sensors 120 may have a raised polygonal shape, circle, semicircle, in, for example, a symmetrical or asymmetrical feature or features. For example, various geometries may be used for use in conjunction with various types of foot coverings, boots, orthotics, and/or cam boots as dimensioned by various manufacturers. Also, the substantial geometric configuration may be of a uniform height, or a portion of the uppermost edge 2 of the sensor 120 may be raised or in such a fashion that the sensor 120 may appear in an angular orientation with respect to the second member 130. Each of the plurality 127 of sensors 120 may be further configured to associate to the first member 110 such that at least one edge 4 of each of the plurality 127 of sensors 120 may maintain close proximity or even direct contact with the top surface 110A of the first member 110. The plurality 127 of sensors 120 may be of any desired number and orientation. In use, under the predetermined threshold and/or when the predetermined threshold of weight is exceeded, the plurality 127 of sensors 120 maintain an amount of displacement between the first member 110 and the second member 130. The second member 130 may be configured to associate to the plurality of sensors 127 in a manner previously described.

The apparatus 100 described herein may further include an alarm, which may be used either with the snapping feature of the sensor or the alarm may be used alone. The alarm may be configured to associate to the at least two sensors 120 to provide a detectable feedback if, for example, a predetermined mechanical force threshold is exceeded on at least one of the plurality 127 of sensors 120. The alarm may be selected from the group consisting of: a tactile alarm, an acoustic alarm, an audible alarm, a visible alarm, a thermal alarm, and one or more combinations thereof.

The apparatus 100 described herein may additionally serve as a locomotion monitoring apparatus.

The base member 115 of the gait-response apparatus 105 may be configured to associate to the plurality of sensors 127 such that at least one edge of each of the plurality of sensors 127 may maintain contact with or close proximity to the base member 115. The base member may be composed or included of one or more materials such that the base member may provide a sturdy, durable surface for the plurality of sensors 127 to associate to and otherwise work against in operation. The base member 115 may be of a size, shape, orientation, and dimension such that the base member 115 may be operable along and about a subject or user's foot.

Figure 7:
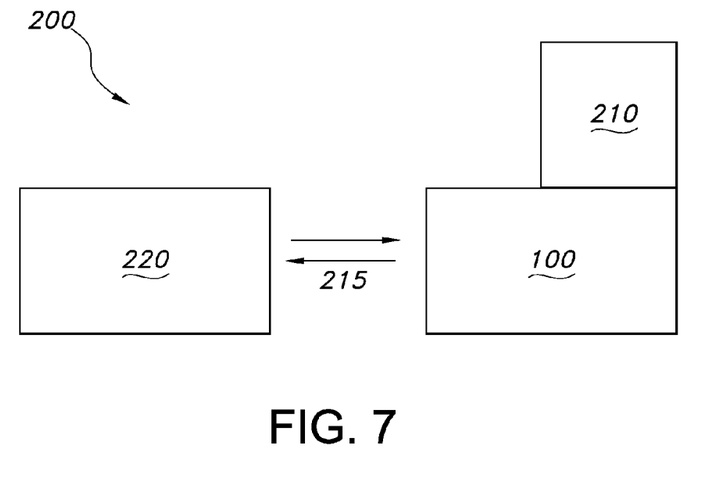
FIG. 7 depicts an example of an embodiment of the a weight monitoring system of the present invention.
Figure 10:
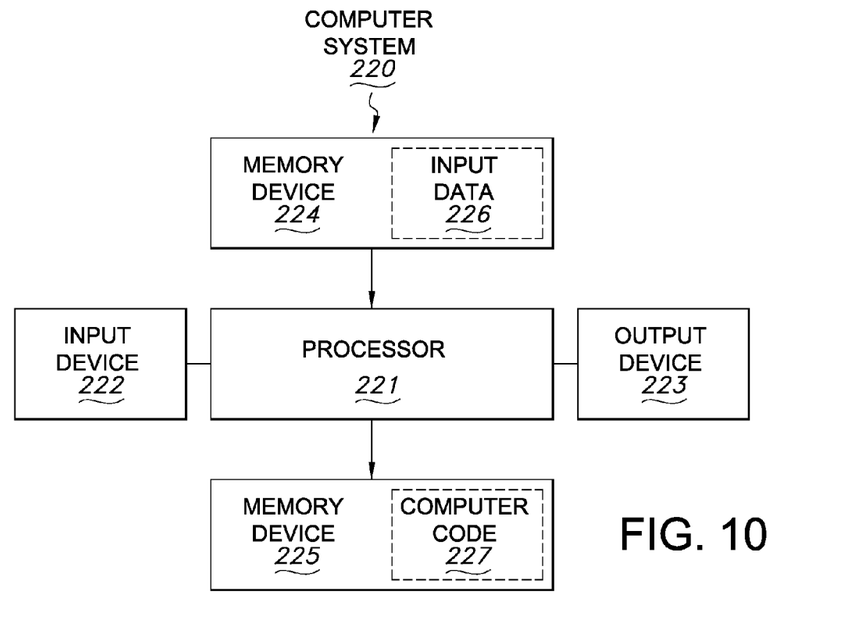
FIG. 10 depicts an exemplary diagram of a computer system of an embodiment of a system of the present invention.

Still yet another aspect of the present invention includes a weight monitoring system 200 as represented by FIGS. 7 and 10. The weight monitoring system 200 may include, for example, a weight monitoring apparatus 100, an optional foot covering 210, and an analysis system 220. The foot covering 210 may be configured to associate to a user's foot. The user's foot may include, for example, the natural body part, a modified body part, or a prosthetic foot. The foot may be of a given shape, size, dimension, and orientation, and thus, the foot covering 210 may be configured to provide support and comfort to any given foot. The weight monitoring apparatus 100 may be configured to insert into the foot covering 210, or it may be manufactured as an integral component of the foot covering 210, and operatively associate between the user's foot and a surface of the foot covering 210. The weight monitoring apparatus 100 may be configured to transmit at least one measurement datum 215 to the analysis system 220. The weight monitoring apparatus 100 may be of the features and elements described and disclosed supra. The measurement datum 215 may include a datum selected from the group consisting of: a load datum, an alarm excess datum, a lower threshold alarm, a multiple sensor alarm, a toe-strike heel-off time or pressure measurement, and combinations thereof.

The analysis system 220 may include any mechanism to gather and analyze the datum 215 generated by the weight monitoring system 200. In one embodiment, the analysis system 220 may include simple note-taking methods and human analysis. In another embodiment, the analysis system 220 may be a computer-based analysis system. The computer-based analysis system 220 may be operably associated with the weight monitoring apparatus 100 and configured to receive at least one measurement datum 215 therefrom. The sensors 120 of the weight monitoring apparatus 100 may include a transmitter. The transmitter may transmit an alarm or signal to a user as a result of an exceeded weight limit on one or more sensors as an electrical or radiofrequency signal to a computer-based analysis system 220.

One embodiment of the computer-based analysis system 220 is depicted in FIG. 10. The computer-based analysis system 220 may include, for example, a processor and a computer readable memory unit coupled to the processor, the memory unit containing instructions that when executed by the processor implement a method. The computer-based analysis system 220 may include a processor 221, an input device 222 coupled to the processor 221, an output device 223 coupled to the processor 221, and memory devices 224 and 225 each coupled to the processor 221. The memory device 225 may include computer code 227. In another embodiment, a memory device 224 may include input data 226. Each of the features of the computer-based analysis system 220 may include additional features that may be understood by one of skill in the art.

Figure 8:
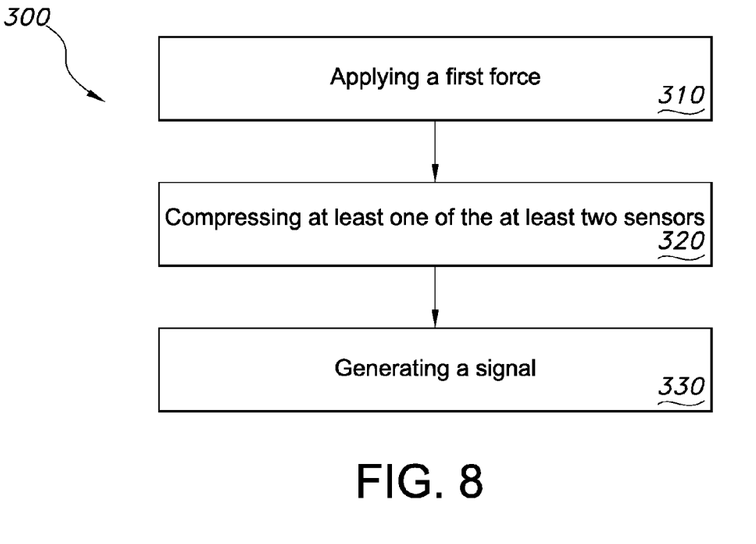
FIG. 8 depicts an example of an embodiment of a therapeutic load monitoring method of the present invention.

Still yet another aspect of the present invention includes a therapeutic method 300 as set forth in FIG. 8. The therapeutic method 300 may include, for example, applying a first force 310 to a weight monitoring apparatus, compressing at least one of two sensors of the weight monitoring apparatus 320, and generating a signal by the compression of at least one of the two sensors 330. The therapeutic method 300 may first include applying a first force to a weight monitoring apparatus 310. The first force 310 may be a weight, a load, or an angular force. The weight monitoring apparatus 100 may be of the features and elements described and disclosed supra. The therapeutic method 300 may further include compressing at least one of the at least two sensors of the weight monitoring apparatus by the first force, the first force exceeding a threshold level of the at least two sensors 320. The threshold level may be a weight or pressure limit set by a clinician, physician, researcher, physical therapist, health care professional, technician, or other person. The threshold level may be an upper limit of weight that a subject or user should exert pursuant to a therapy, treatment, or other instruction. The threshold level may change over time, such that, for example, a user or subject may place more load or weight on their foot or a part thereof as time progresses and an injury, ailment, or limitation may otherwise be alleviated or ameliorated. In some embodiments, the threshold level may be an exertion of anywhere from 10-50% of the normal pressure generated by the user when walking, and more specifically may be about 20-30% of the normal pressure generated by the user when walking.

After the compressing step, the therapeutic method 300 may include generating a signal 330 by the compression of one of the at least two sensors. In such a manner, the user may be advised, alerted, signaled, or otherwise informed that they have exerted or otherwise placed too much pressure, load, or weight upon one or more of the at least two sensors 120 of the weight monitoring apparatus 100. The signal 330 generated may be as a function of the design and operation of the compression of at least one of the two sensors 120. For example, the signal 330 may be an audible, tactile, acoustic, or visual signal generated to or on the user or subject foot or lower extremity.

Figure 9:
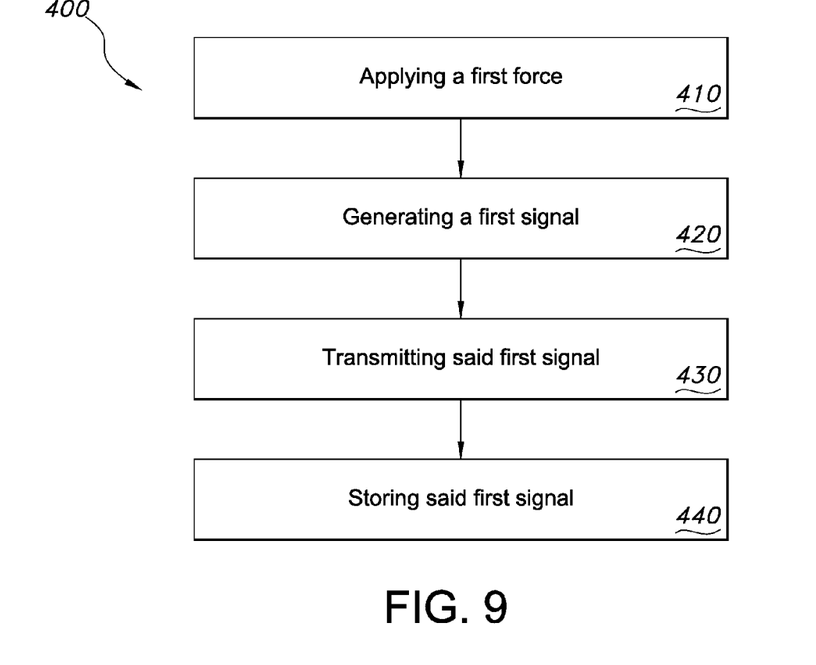
FIG. 9 depicts an example of an embodiment of a therapeutic load computerized monitoring method of the present invention.

Further still another aspect of the present invention includes a therapeutic method 400 as described in FIG. 9. The therapeutic method 400 may include, for example, the steps of applying a first force 410 to a weight monitoring apparatus, generating a first signal 420 from the first force, transmitting the first signal 430, and storing the first signal 440.

Applying a first force to a weight monitoring apparatus 410 may include, for example, applying a user or subject weight, or a portion thereof, onto the weight monitoring apparatus 410 in a detectable manner, such as a subject stepping on the weight monitoring apparatus using the subject's foot. The weight monitoring apparatus 100 may be of the features and elements described supra. After applying a first force 410, the therapeutic method 400 may include: generating a first signal by the weight monitoring system in response to the first force 420. As previously stated, the signal may be tactile, acoustic, audible, visual, or a combination thereof. The signal may be generated such that a subject or user, observer, or a combination thereof may observe the signal generated. Also, the signal may be generated as an electrical signal. The therapeutic method 400 may further include transmitting the first signal from the weight monitoring apparatus to a computer system configured to receive the first signal. The computer system may be of the features and elements of the computer system described supra. The therapeutic method 400 may further include storing the first signal in the computer system. The first signal may be stored in, for example, a hard drive, a software program, one of more memory devices, or one or more input or output devices of the computer system. The therapeutic method may be reiterated such that a plurality of signals may be generated, transmitted, and recorded or stored as data onto one or more parts of the computer system. One or more programs or output devices of the computer system may aid in, for example, analysis, manipulation, devising of treatment plans, therapy plans, and combinations thereof, utilizing the stored plurality of signals. It should be noted that one or more of the various exemplary embodiments of the present invention may be manufactured as a stand-alone apparatus or as a replacement for a cam boot foam insert.

Figure 11:
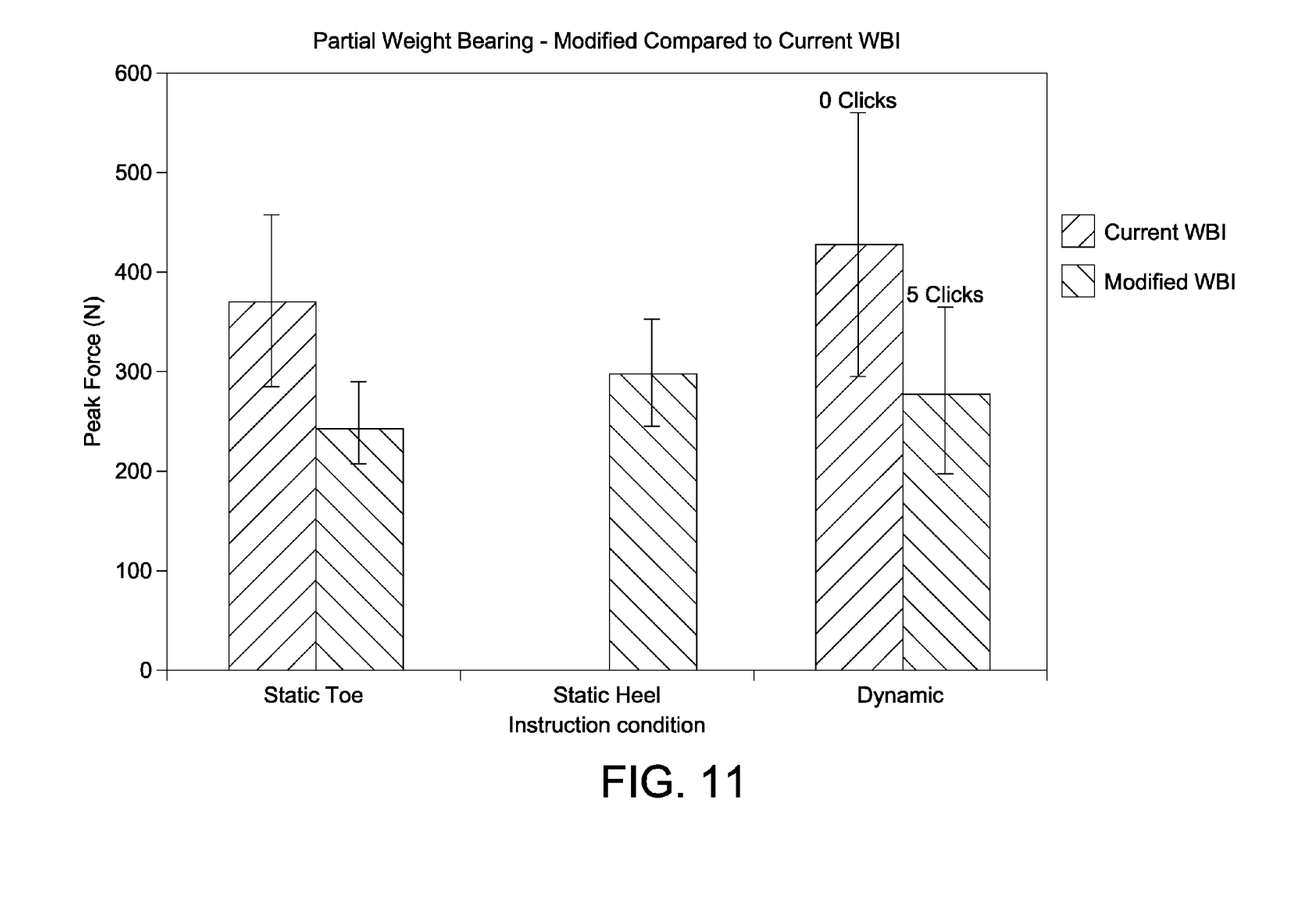
FIG. 11 depicts a chart illustrating a comparative analysis of the benefits and advantages of the present invention compared to another device.

As may be seen in FIG. 11, the present invention provides an improved weight monitoring design than that currently in use today. The apparatus of the present invention (labeled "Modified WBI") generated better feedback at lower forces than the current weight bearing instruments in use today for static toe, static heel, and dynamic instructions.

Various modifications and variations of the described apparatus and methods of the invention will be apparent to those skilled in the art without departing from the scope and spirit of the invention. Although the invention has been described in connection with specific embodiments, outlined above, it should be understood that the invention should not be unduly limited to such specific embodiments. Various changes may be made without departing from the spirit and scope of the invention as defined.

The invention described herein may be more fully understood from the following, non-limiting examples.

EXAMPLES

Example 1

Device Evaluation

Three groups of subjects were evaluated to determine the effect of the inventive indicator apparatus. A first group of subjects having surgically treated ankle fractures were asked to perform gait with verbal instruction only. A second group of subjects were asked to perform gait while using a prior art (single-button) weight monitoring device. The third group of subjects was asked to perform gait with the inventive (full-sole) weight monitoring apparatus described herein. All subjects were provided IRB-approved informed consent and were fitted with crutches and a cam boot on the affected limb.

For the first group, the subjects were verbally instructed to limit the weight put on their subject foot to 130 N or less, but were given no further instruction. In the second group (utilizing the prior art indicator device), an effective 130 N indicator device that gave an audible/tactile click when the force threshold was exceeded was inserted under the ball of the foot in the cam boot sole. The subject was allowed to practice walking with the indicator device with the goal of not allowing the device to click. In the third group (using the inventive apparatus), the foam sole of the standard cam boot was replaced with a full-sole insert with snap dome devices in the toe and the heel, and further including the first member, second member, and the support bar described above.

The test protocol for these groups consisted of five trials of ambulating with crutches and the provided cam boot over a ten meter walkway at a comfortable pace. Force-time history data of a single cam boot foot strike was collected for each trial from a force plate embedded into the walkway. The peak load from each force-time history was determined.

Figure 12:
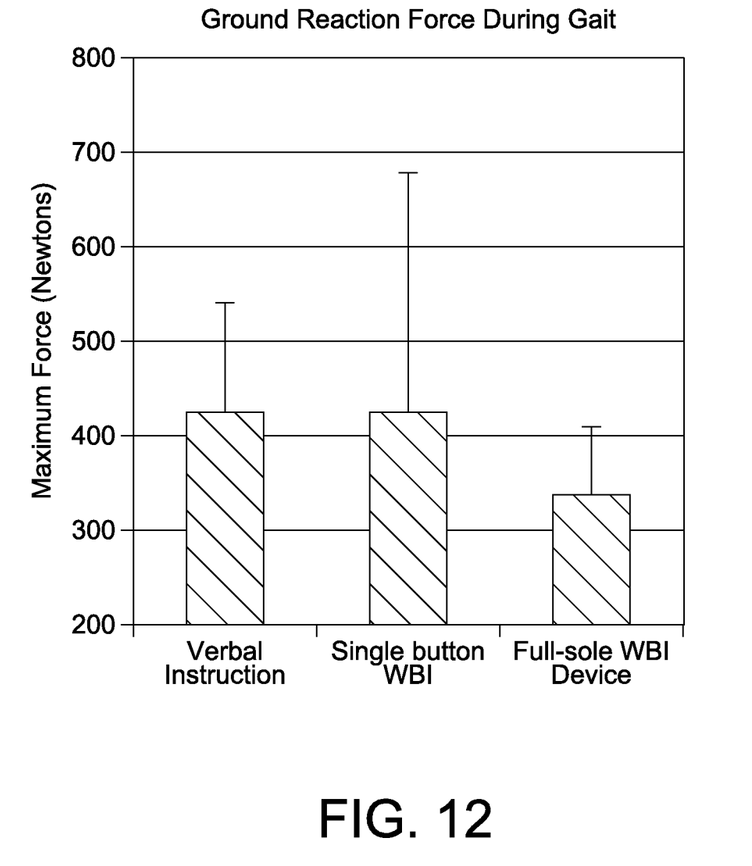
FIG. 12 depicts the results of a device evaluation study.

The results are indicated in FIG. 12. As can be seen, the subjects who were given only verbal instruction performed no better statistically than those subjects using the prior art, single-button indicator. In fact, it was determined that the subjects using the prior art single-button indicator device had a much higher variance in force, indicating that uniform results would be less likely to occur by using this device configuration. In addition, none of the prior art single-button devices registered an audible click, which would have indicated that the force was exceeded, despite the high loads exerted by the subjects.

In contrast, the subjects using the inventive indicator apparatus performed better (i.e., a lower force) and also demonstrated a much lower variance in the response. During loading trials, the inventive indicator apparatuses demonstrated four audible clicks, indicating that the subjects were placing too much force on the device.

It was evident from the gait patterns that the subjects with the prior art single-button indicator device were loading their feet during both heel strike and during toe-off, while the device can only detect fore-foot loading (i.e., towards toe-off). Thus, the results clearly demonstrate significantly higher success and a more effective weight-monitoring apparatus than that in the prior art.

What is claimed is:

1. A weight monitoring apparatus for wearing on a foot of a user, comprising:
   a. a rigid first member having a length and width sized to be larger than the length and width of said foot, and having a top surface, said rigid first member designed to be a stable and stiff base that is unyielding when a load is applied thereon;
   b. a second member having a length and width sized to be larger than the length and width of said foot, and having a top surface and a bottom surface;
   c. a first sensor disposed between and configured to associate with the top surface of the first member and the bottom surface of the second member and disposed at a location proximal to a toe region of said foot;
   d. a second sensor disposed between and configured to associate with the top surface of the first member and the bottom surface of the second member and disposed at a location proximal to a heel region of said foot; and
   e. a support bar disposed between and in contact with the top surface of the first member and the bottom surface of the second member, and disposed at a location between the first and second sensors,
   wherein the support bar functions as a fulcrum for the second member when the load is applied to the top surface of the second member allowing for angular load transfer to the first or the second sensor.

2. The apparatus of claim 1, wherein one of said sensors is a mechanical sensor.

3. The apparatus of claim 2, wherein one of said sensors is a dome-shaped sensor.

4. The apparatus of claim 1, wherein said apparatus is capable of being inserted into footwear.

5. The apparatus of claim 1, wherein said apparatus comprises a cam boot.

6. The apparatus of claim 1, wherein at least one of said sensors provides a detectable feedback to a user if a predetermined mechanical force threshold is exceeded on at least one of said sensors.

7. The apparatus of claim 2, wherein said dome-shaped sensor is a snap-dome sensor.

8. The apparatus of claim 6, wherein said detectable feedback is one of audible, visual and tactile.

9. The apparatus of claim 8, wherein said detectable feedback is audible.

10. The apparatus of claim 8, wherein said detectable feedback is tactile.

11. The apparatus of claim 1, wherein said first and second members are flat.

12. The apparatus of claim 1, wherein said first member substantially conforms to an inner bottom portion of footwear.

13. The apparatus of claim 12, wherein said footwear is one of a shoe, a boot, a cast, a walking cast, a brace, or a cam boot.

14. The apparatus of claim 13, wherein said footwear is a cam boot.

15. The apparatus of claim 12, wherein said apparatus is a replacement for the foam insert of a cam boot.

16. The apparatus of claim 1, wherein at least one of said sensors generates an electrical signal.

17. The apparatus of claim 1, wherein at least one of said sensors generates a radio-frequency signal.

18. The apparatus of claim 6, wherein said predetermined mechanical force threshold is between ten and fifty percent of the normal pressure generated by a user when walking.

19. The apparatus of claim 6, wherein said predetermined mechanical force threshold is between twenty and thirty percent of the normal pressure generated by a user when walking.

20. The apparatus of claim 6, wherein said predetermined mechanical force threshold is 130 newtons or less.

21. The apparatus of claim 1, wherein said second member is semi-rigid.

\* \* \* \* \*